United States Patent
Takeuchi et al.

(10) Patent No.: US 10,792,641 B2
(45) Date of Patent: Oct. 6, 2020

(54) STRUCTURE

(71) Applicant: FUJI XEROX CO., LTD., Tokyo (JP)

(72) Inventors: Sakae Takeuchi, Kanagawa (JP);
Hideaki Yoshikawa, Kanagawa (JP);
Hiroyoshi Okuno, Kanagawa (JP);
Yasunobu Kashima, Kanagawa (JP);
Takeshi Iwanaga, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 96 days.

(21) Appl. No.: 16/116,934

(22) Filed: Aug. 30, 2018

(65) Prior Publication Data
US 2019/0255515 A1 Aug. 22, 2019

(30) Foreign Application Priority Data
Feb. 22, 2018 (JP) ................. 2018-029995

(51) Int. Cl.
| | | |
|---|---|---|
| *B01J 21/06* | (2006.01) | |
| *C09D 7/61* | (2018.01) | |
| *C09D 7/40* | (2018.01) | |
| *C09D 183/04* | (2006.01) | |
| *C09D 5/16* | (2006.01) | |
| *A61L 9/20* | (2006.01) | |
| *B01J 31/06* | (2006.01) | |
| *B01J 35/00* | (2006.01) | |
| *B01J 35/10* | (2006.01) | |
| *B01J 31/38* | (2006.01) | |
| *C08K 3/22* | (2006.01) | |

(52) U.S. Cl.
CPC ............ *B01J 21/063* (2013.01); *A61L 9/205* (2013.01); *B01J 31/06* (2013.01); *B01J 31/38* (2013.01); *B01J 35/004* (2013.01); *B01J 35/0013* (2013.01); *B01J 35/1019* (2013.01); *B01J 35/1023* (2013.01); *B01J 35/1028* (2013.01); *C08K 3/22* (2013.01); *C09D 5/1618* (2013.01); *C09D 5/1675* (2013.01); *C09D 7/61* (2018.01); *C09D 7/67* (2018.01); *C09D 183/04* (2013.01)

(58) Field of Classification Search
CPC . B01J 21/063; B01J 31/06; B01J 31/38; B01J 35/0013; B01J 35/004; B01J 35/1019; B01J 35/1023; B01J 35/1028; C09D 7/61; C09D 7/67; C09D 5/1618; C09D 5/1675; C09D 183/04; A61L 9/205; C08K 3/22
USPC .................. 502/158, 350; 106/286.4, 287.19
See application file for complete search history.

(56) References Cited

U.S. PATENT DOCUMENTS

| | | | |
|---|---|---|---|
| 5,411,761 A | 5/1995 | Inokuchi et al. | |
| 2002/0187338 A1* | 12/2002 | Tanaka ................. | B01J 21/063 428/336 |
| 2003/0181329 A1* | 9/2003 | Tanaka ................. | B01J 21/063 502/338 |
| 2004/0067849 A1* | 4/2004 | Tanaka ................. | B01J 21/063 502/350 |
| 2006/0162617 A1* | 7/2006 | Tanaka ................. | B01J 35/004 106/436 |
| 2010/0298120 A1* | 11/2010 | Tanaka ................. | B01J 21/063 502/159 |
| 2018/0161764 A1* | 6/2018 | Okuno .................. | B01J 21/063 |
| 2018/0162887 A1* | 6/2018 | Okuno .................. | C07F 7/28 |
| 2018/0280953 A1* | 10/2018 | Iwanaga ............... | B01J 31/38 |
| 2018/0311656 A1* | 11/2018 | Yoshikawa ........... | B01J 31/38 |
| 2019/0224648 A1* | 7/2019 | Yoshikawa ........... | B01J 21/06 |

FOREIGN PATENT DOCUMENTS

| | | |
|---|---|---|
| JP | H05221640 | 8/1993 |
| JP | 2001269573 | 10/2001 |
| JP | 2004115541 | 4/2004 |
| JP | 2007016111 | 1/2007 |
| JP | 2010006629 | 1/2010 |

* cited by examiner

*Primary Examiner* — Patricia L. Hailey
(74) *Attorney, Agent, or Firm* — JCIPRNET

(57) ABSTRACT

A structure includes a base material; a surface layer that contains a binder resin and a titanium compound particle having absorption at 450 nm and 750 nm in a visible absorption spectrum and a BET specific surface area within a range of 100 m²/g to 1200 m²/g.

19 Claims, No Drawings

STRUCTURE

CROSS-REFERENCE TO RELATED APPLICATIONS

This application is based on and claims priority under 35 USC 119 from Japanese Patent Application No. 2018-029995 filed Feb. 22, 2018.

BACKGROUND

(i) Technical Field

The present invention relates to a structure.

(ii) Related Art

For example, JP2004-115541A discloses a silica-coated titanium oxide powder. For example, JP2001-269573A discloses a titanium oxide particle having a part of a surface to which a porous coating layer formed of fine ceramic particles is fixed. For example, JP2007-16111A discloses a silica-coated titanium oxide particle. For example, JP2010-6629A discloses a high-density silica- and porous silica-coated titanium oxide particle. For example, JP1993-221640A discloses a titanium oxide particle having a film of a product of trialkoxysilane hydrolysis and condensation.

SUMMARY

An aspect of non-limiting exemplary embodiments of the present disclosure relates to a structure including a base material; and a surface layer that contains a binder resin and a titanium compound particle having absorption at 450 nm and 750 nm in a visible absorption spectrum, the structure having a photolysis function by visible light and an excellent adsorption property, compared to a case in which a particle having a BET specific surface area of less than 100 $m^2/g$ is merely contained as the particle.

Another aspect of non-limiting exemplary embodiments of the present disclosure relates to a structure including a base material; and a surface layer that contains a binder resin and a particle having absorption at 450 nm and 750 nm in a visible absorption spectrum, and that contains a binder resin, the structure having a photolysis function by visible light and a high degree of water repellency, compared to a case in which a water contact angle on a surface of the surface layer is smaller than 90 degrees.

Aspects of certain non-limiting embodiments of the present disclosure overcome the above disadvantages and other disadvantages not described above. However, aspects of the non-limiting embodiments are not required to overcome the disadvantages described above, and aspects of the non-limiting embodiments of the present disclosure may not overcome any of the problems described above.

According to an aspect of the present disclosure, there is provided a structure including a base material; and a surface layer that contains and a binder resing and a titanium compound particle having absorption at 450 nm and 750 nm in a visible absorption spectrum and a BET specific surface area is within a range of 100 $m^2/g$ to 1200 $m^2/g$.

DETAILED DESCRIPTION

Hereinafter, an exemplary embodiment of the invention will be described.

In a case where plural kinds of substances corresponding to each component in the composition are present, a case of mentioning an amount of each component in a composition in the present disclosure means a total amount of the plural kinds of substances present in the composition, unless otherwise specified.

In the present disclosure, in regard to the term "step", not only an independent step but also a step which is not clearly distinguishable from other steps is included in this term as long as an intended purpose of the step may be achieved.

Structure According to First Exemplary Embodiment

A structure according to a first exemplary embodiment includes a base material and a surface layer.

The surface layer contains a binder resin and a particle, and this particle is a titanium compound particle having absorption at 450 nm and 750 nm in a visible absorption spectrum and a BET specific surface area is from 100 $m^2/g$ to 1200 $m^2/g$.

According to the structure according to the first exemplary embodiment, a photolysis function by visible light is exhibited. It is presumed that a reason for this is because the particle exhibits a light absorption property at wavelengths of 450 nm and 750 nm, and the particle expresses visible-light responsiveness.

In addition, excellent adsorption property is exhibited, and thus the structure according to the first exemplary embodiment is excellent in, for example, a deodorizing property or the like. It is considered that in the first exemplary embodiment, in regard to the particle having the BET specific surface area of 100 $m^2/g$ or larger (titanium compound particle), many pores and voids are contained in the particle, and thus excellent adsorption property may be obtained, compared to the titanium compound particle of the related art.

BET Specific Surface Area

For example, the BET specific surface area of the particle in the first exemplary embodiment is from 100 $m^2/g$ to 1200 $m^2/g$, preferably from 150 $m^2/g$ to 1100 $m^2/g$, and more preferably from 200 $m^2/g$ to 1000 $m^2/g$.

With the BET specific surface area of the particle being 100 $m^2/g$ or larger, excellent adsorption property is exhibited, and with the BET specific surface area being 1200 $m^2/g$ or smaller, a proportion of coarse particles (for example, the particles having a particle diameter of larger than 20 μm) decreases, and therefore particle dispersibility is likely to be improved in the structure as a photocatalyst, and a high degree of a photocatalytic function is likely to be expressed.

The BET specific surface area of the particle in the first exemplary embodiment is obtained by a gas adsorption method using nitrogen gas. Details of a measurement method are as described in a section of "Examples" to be described below.

Particle in First Exemplary Embodiment

In the first exemplary embodiment, the titanium compound particle is used as a particle to be contained in the surface layer. In the present disclosure, the term "titanium compound particle" does not include a particle having an aerogel shape (that is, a titanium compound aerogel particle).

Examples of the titanium compound particle include a metatitanic acid particle, a titanium oxide particle, and a strontium titanate.

Among these, for example, the metatitanic acid particle and the titanium oxide particle are preferable, and the metatitanic acid particle is more preferable.

Purpose of Structure According to First Exemplary Embodiment

The structure according to the first exemplary embodiment is applied to a purpose in which the adsorption property (specific examples thereof include the deodorizing property) is required, for example. For example, the structure according to the first exemplary embodiment is used as an interior wallpaper, a plaster wall, a tile, and a siding material. Among these, the structure according to the first exemplary embodiment is, for example, preferably used as the interior wallpaper, the tile, and the siding material.

In a case where the structure according to the first exemplary embodiment is used as the interior wallpaper, as the base material of the structure, paper, a woven fabric, a knitted fabric, a nonwoven fabric, a composite material thereof, or the like is used, for example.

In a case where the structure according to the first exemplary embodiment is used as the plaster wall, as the base material of the structure, diatomaceous earth, lime plaster, or the like is used, for example.

In a case where the structure according to the first exemplary embodiment is used as the tile, as the base material of the structure, a ceramic, concrete, plastic, or the like is used, for example.

In a case where the structure according to the first exemplary embodiment is used as the siding material, as the base material of the structure, a base material of a ceramic (ceramic industry), wood, a metal, or the like is used, for example.

Structure of Second Exemplary Embodiment

A structure according to a second exemplary embodiment includes a base material and a surface layer.

The surface layer contains a binder resin and a particle, and this particle is at least one particle selected from the group consisting of a titanium compound particle and a titanium compound aerogel particle having absorption at 450 nm and 750 nm in a visible absorption spectrum.

In addition, a water contact angle on a surface of the surface layer is from 90 degrees to 180 degrees.

According to the structure of the second exemplary embodiment, the photolysis function by visible light is exhibited. It is presumed that a reason for this is because the particle exhibits the light absorption property at wavelengths of 450 nm and 750 nm, and the particle expresses the visible-light responsiveness.

In addition, a high degree of water repellency is exhibited, and thus the structure according to the second exemplary embodiment is excellent in, for example, an antifouling property or the like. It is considered that in the surface layer in which the water contact angle on the surface is 90 degrees or larger in the second exemplary embodiment, the water contact angle on the surface is large, and thus a high degree of the water repellency may be obtained compared to a case of a surface layer containing at least one of a titanium compound particle or a titanium compound aerogel particle of the related art.

Water Contact Angle

For example, the water contact angle of the surface layer of the second exemplary embodiment is from 90 degrees to 180 degrees, preferably from 115 degrees to 180 degrees, and more preferably from 130 degrees to 180 degrees.

With the water contact angle of the surface layer being 90 degrees or larger, a high degree of the water repellency is exhibited, and with the water contact angle of the surface layer being 180 degrees or smaller, adhesion of water to the structure is prevented, and therefore an antifouling effect may be obtained.

Details of a measurement method of the water contact angle of the surface layer in the second exemplary embodiment are as described in the section of "Examples" to be described below.

Particle in Second Exemplary Embodiment

In the second exemplary embodiment, at least one particle selected from the group consisting of the titanium compound particle and the titanium compound aerogel particle is used as the particle to be contained in the surface layer. The term "titanium compound particle" does not include the titanium compound aerogel particle.

Examples of the titanium compound particle include the metatitanic acid particle, the titanium oxide particle, the strontium titanate, and the like.

Examples of the titanium compound aerogel particle include a titanium oxide aerogel particle and a silica-titania aerogel particle.

Among these, as the particle in the second exemplary embodiment, for example, the metatitanic acid particle, the titanium oxide particle, the silica-titania aerogel particle, and the titanium oxide aerogel particle are preferable, and the metatitanic acid particle is more preferable.

Purpose of Structure According to Second Exemplary Embodiment

The structure according to the second exemplary embodiment is applied to a purpose in which the water repellency (specific examples thereof include the antifouling property) is required, for example. For example, the structure according to the second exemplary embodiment is used as the interior wallpaper, the plaster wall, the tile, and the siding material. Among these, the structure according to the second exemplary embodiment is, for example, preferably used as the interior wallpaper, the tile, and the siding material.

In a case where the structure according to the second exemplary embodiment is used as the interior wallpaper, as the base material of the structure, paper, a woven fabric, a knitted fabric, a nonwoven fabric, a composite material thereof, or the like is used, for example.

In a case where the structure according to the second exemplary embodiment is used as the plaster wall, as the base material of the structure, diatomaceous earth, lime plaster, or the like is used, for example.

In a case where the structure according to the second exemplary embodiment is used as the tile, as the base material of the structure, a ceramic, concrete, plastic, or the like is used, for example.

In a case where the structure according to the second exemplary embodiment is used as the siding material, as the base material of the structure, a base material of a ceramic, wood, a metal, or the like is used, for example.

Accomplishment Method

Although there is no particular limitation, the structure according to the first exemplary embodiment including the surface layer that contains the particle (titanium compound particle) having the BET specific surface area within the above-described range, is achieved by, for example, forming a surface layer on a base material by using a particle manufactured according to "a method for manufacturing a titanium compound particle" to be described below.

In addition, although there is no particular limitation, the structure of the second exemplary embodiment including the surface layer in which the water contact angle on the surface is within the above-described range, is achieved by, for example, forming a surface layer on a base material according to "a method for forming a surface layer" to be described below.

Hereinafter, constitutions of the structures according to the first exemplary embodiment and the second exemplary embodiment will be described in more details.

A case in which both the first exemplary embodiment and the second exemplary embodiment are referred to, will simply be referred to as "this exemplary embodiment."

Constitution of Structure

The structure according to the first exemplary embodiment and the second exemplary embodiment (this exemplary embodiment) includes the base material and the surface layer that contains the binder resin and the particle in having absorption at 450 nm and 750 nm in a visible absorption spectrum.

The titanium compound particle is used as the particle in the first exemplary embodiment, and at least one particle selected from the group consisting of the titanium compound particle and the titanium compound aerogel particle is used as the particle in the second exemplary embodiment.

Surface Layer of the Particle

As the particle having absorption at 450 nm and 750 nm in a visible absorption spectrum used in this exemplary embodiment, a particle in which a metallic compound having a metal atom and a hydrocarbon group is bonded to a surface via an oxygen atom is, for example, preferable (the titanium compound particle or the titanium compound aerogel particle). The particle in which the metallic compound having a metal atom and a hydrocarbon group is bonded to the surface via an oxygen atom may be obtained by surface-treating an untreated particle (an untreated titanium compound particle or an untreated titanium compound aerogel particle) by the metallic compound having a hydrocarbon group, and then oxidizing at least a part of the hydrocarbon group by a heating treatment so as to be changed to a C—O bond or a C═O bond. A detailed mechanism thereof is unclear, but it is presumed that with a presence of, on the surface of the particle, a structure in which an organometallic compound in which a carbon atom is appropriately oxidized, an oxygen atom, and a titanium atom (or a silicon atom) are sequentially linked by a covalent bond, the particle surface shows the light absorption property at wavelengths of 450 nm and 750 nm, and the particle expresses the photolysis function by visible light (visible-light responsiveness).

Hereinafter, the metallic compound having a metal atom and a hydrocarbon group will simply be referred to as "organometallic compound."

The organometallic compound which is bonded to the surface of the particle via an oxygen atom in this exemplary embodiment is, for example, preferably a metallic compound formed of only a metal atom, a carbon atom, a hydrogen atom, and an oxygen atom, from a viewpoint of more easily expressing the visible-light responsiveness.

The metallic compound which is bonded to the surface of the particle via an oxygen atom in this exemplary embodiment is, for example, preferably bonded to the surface of the particle via an oxygen atom O that is directly bonded to a metal atom M in the metallic compound, that is, preferably bonded to the surface of the particle via a covalent bond of M-O—Ti or M-O—Si, from the viewpoint of more easily expressing the visible-light responsiveness.

In the particle in this exemplary embodiment, for example, it is preferable that the metallic compound having a metal atom and a carbon atom directly bonded to the metal atom is bonded to the surface via an oxygen atom, from the viewpoint of more easily expressing the visible-light responsiveness. It is presumed that with a condition in which a structure (C-M-O—Ti (or C-M-O—Si)) in which a carbon atom C, a metal atom M, an oxygen atom O, and a titanium atom Ti (or a silicon atom Si) are sequentially linked by a covalent bond, is present on the surface of the particle, and the carbon atom C is appropriately oxidized, the particle surface shows the light absorption property at wavelengths of 450 nm and 750 nm, and the particle expresses the visible-light responsiveness.

In the particle in this exemplary embodiment, as the metal atom M constituting the organometallic compound bonded to the surface of the particle via an oxygen atom, for example, a metal atom selected from the group consisting of silicon, aluminum, and titanium is preferable, and a metal atom selected from the group consisting of silicon and aluminum is more preferable, and silicon is particularly preferable.

The particle in this exemplary embodiment is, for example, also preferable from the following viewpoint, in addition to a high level of the photocatalytic function expressed in a visible light region.

Generally, an untreated particle (an untreated titanium compound particle or an untreated titanium compound aerogel particle) has a low degree of freedom in controlling a particle diameter, a particle size distribution, and a particle shape, and a particle agglomerating property tends to be high. Therefore, dispersibility of the particles in a resin or a liquid is poor, and there is a tendency that 1) the photocatalytic function is unlikely to be exhibited, 2) homogeneity of a coated film of an application solution low, and 3) transparency of a film and the like is low.

On the other hand, the particle in this exemplary embodiment having, on the surface thereof, a hydrocarbon group derived from the metallic compound, makes the dispersibility preferable, for example. Therefore, a coated film that is almost homogenous may be formed, light efficiently reaches the particles, and thus the photocatalytic function becomes likely to be exhibited. In addition, the transparency of a film and the like and the homogeneity of the coated film in the application solution are also improved, and therefore designability is also maintained. As a result, for example, in a case of coating a surface of an outer wall material, a plate, a pipe, or a nonwoven fabric (nonwoven fabric such as a ceramic) with a paint containing the particles, an agglomeration or a coating defect of the particles is suppressed, and the photocatalytic function becomes likely to be exhibited for a long period of time.

Untreated Particle

In the present disclosure, the particle which has not been subjected to a surface treatment by the metallic compound having a metal atom and a hydrocarbon group (organometallic compound) is referred to as the "untreated particle."

As examples of the untreated particle used in this exemplary embodiment, the untreated titanium compound particle (an untreated metatitanic acid particle, an untreated titanium oxide particle, or the like), and the untreated titanium compound aerogel particle (an untreated silica-titania aerogel particle, an untreated titanium oxide aerogel particle, or the like) are preferable, for example.

In the first exemplary embodiment, the untreated titanium compound particle is used as the untreated particle, and in the second exemplary embodiment, at least one particle selected from the group consisting of the untreated titanium compound particle and the untreated titanium compound aerogel particle is used as the untreated particle.

Hereinafter, using these as examples, the untreated particle will be described.

Untreated Titanium Compound Particle: Untreated Titanium Oxide Particle

In the present disclosure, the titanium oxide particle which has not been subjected to the surface treatment by the organometallic compound will be referred to as the "untreated titanium oxide particle." Examples of the untreated titanium oxide particle (the titanium oxide particle which is a target of the surface treatment) include a particle of a titanium oxide such as a brookite type, an anatase type, and a rutile type. The titanium oxide particle may have a single crystal structure such as brookite, anatase, rutile, or the like and may have a mixed-crystal structure in which these crystals coexist.

The untreated titanium oxide particle in this exemplary embodiment is the titanium oxide particle which has not been subjected to the surface treatment by the organometallic compound, and it is needless to say that other surface treatments are excluded, but the titanium oxide particle in this exemplary embodiment is, for example, preferably a titanium oxide particle which has been subjected to the surface treatment only by the organometallic compound.

A method for manufacturing the untreated titanium oxide particle is not particularly limited, and examples thereof include a chlorine method (gas phase method) and a sulfuric acid method (liquid phase method).

An example of the chlorine method (gas phase method) is as follows. First, rutile ore of a raw material is reacted with coke and chlorine and once formed into a gaseous titanium tetrachloride, and then cooled to obtain liquid titanium tetrachloride. Next, the liquid titanium tetrachloride is reacted with oxygen at a high temperature, and then chlorine gas is separated, and therefore an untreated titanium oxide is obtained.

An example of the sulfuric acid method (liquid phase method) is as follows. First, ilmenite ore ($FeTiO_3$) or titanium slag of a raw material is dissolved in concentrated sulfuric acid, an iron component as an impurity is separated as iron sulfate ($FeSO_4$), and once formed into titanium oxysulfate ($TiOSO_4$). Next, titanium oxysulfate ($TiOSO_4$) is hydrolyzed and precipitated as titanium oxyhydroxide ($TiO(OH)_2$). Next, this precipitate is washed and dried, the dried product is calcined, and therefore an untreated titanium oxide is treated.

Other examples of the method for manufacturing the untreated titanium oxide particle include a sol-gel method using titanium alkoxide, a method of calcining metatitanic acid, or the like. Because a crystal structure of the titanium oxide particle changes into brookite, anatase, and rutile in accordance with a degree of a calcination temperature (heating at a range of 400° C. to 1,200° C. for example), and therefore by adjusting a degree of the calcination temperature, the titanium oxide particle having a desired crystal structure may be obtained.

Untreated Titanium Compound Particle: Untreated Metatitanic Acid Particle

In the present disclosure, the metatitanic acid particle which has not been subjected to the surface treatment by the organometallic compound will be referred to as the "untreated metatitanic acid particle." The untreated metatitanic acid particle (the metatitanic acid particle which is a target of the surface treatment) refers to a particle of titanic acid of n=1 of a titanic acid hydrate $TiO_2 \cdot nH_2O$.

The untreated metatitanic acid particle in this exemplary embodiment is the metatitanic acid particle which has not been subjected to the surface treatment by the organometallic compound, and it is needless to say that other surface treatments are excluded, but the metatitanic acid particle in this exemplary embodiment is, for example, preferably a metatitanic acid particle which has been subjected to the surface treatment only by the organometallic compound.

A method for manufacturing the untreated metatitanic acid particle is not particularly limited, and examples thereof include a chlorine method (gas phase method) and a sulfuric acid method (liquid phase method).

An example of the chlorine method (gas phase method) is as follows. First, rutile ore of a raw material is reacted with coke and chlorine and once formed into a gaseous titanium tetrachloride, and then cooled to obtain liquid titanium tetrachloride. Next, the titanium tetrachloride is dissolved in water, and is hydrolyzed while charging a strong base in the mixture, and therefore an untreated metatitanic acid [titanium oxyhydroxide ($TiO(OH)_2$)] particle may be obtained.

An example of the sulfuric acid method (liquid phase method) is as follows. First, ilmenite ore ($FeTiO_3$) or titanium slag of a raw material is dissolved in concentrated sulfuric acid, an iron component as an impurity is separated as iron sulfate ($FeSO_4$), and once formed into titanium oxysulfate ($TiOSO_4$) (titanyl sulfate solution). Next, titanium oxysulfate ($TiOSO_4$) is hydrolyzed, and therefore an untreated metatitanic acid [titanium oxyhydroxide ($TiO(OH)_2$)] particle may be obtained.

Untreated Titanium Compound Aerogel Particle: Untreated Titanium Oxide Aerogel Particle In the present disclosure, the titanium oxide aerogel particle which has not been subjected to the surface treatment by the organometallic compound will be referred to as the "untreated titanium oxide aerogel particle."

The untreated titanium oxide aerogel particle is the titanium oxide aerogel particle which has not been subjected to the surface treatment by the organometallic compound, and other surface treatments are excluded. The untreated titanium oxide aerogel particle in this exemplary embodiment is, for example, preferably a titanium oxide aerogel particle which has been subjected to neither the surface treatment by the organometallic compound nor other surface treatments.

A BET specific surface area of the untreated titanium oxide aerogel particle is, for example, preferably from 120 $m^2/g$ to 1000 $m^2/g$, more preferably from 150 $m^2/g$ to 900 $m^2/g$, and even more preferably from 180 $m^2/g$ to 800 $m^2/g$, from a viewpoint of expressing a high level of the photocatalytic function.

An average primary particle diameter of the untreated titanium oxide aerogel particle is, for example, preferably from 1 nm to 120 nm, more preferably from 5 nm to 100 nm, and even more preferably from 10 nm to 90 nm, from the viewpoint of expressing a high level of the photocatalytic function.

A volume average particle diameter of the untreated titanium oxide aerogel particle is, for example, preferably from 0.1 μm to 3 μm, more preferably from 0.3 μm to 2.8 μm, and even more preferably from 0.5 μm to 2.5 μm.

A method for manufacturing the untreated titanium oxide aerogel particle is not particularly limited, but from a viewpoint of controlling a range of the BET specific surface area to be within the above-described range, a sol-gel method using titanium alkoxide as a material is preferable, for example. In regard to the titanium oxide aerogel particle manufactured by the sol-gel method, primary particles agglomerate in a dispersion to form porous particles having a porous structure (porous particles containing titanium oxide), and thus the BET specific surface area within the above-described range may be realized.

The untreated titanium oxide aerogel particle is preferably formed of a hydrolytic condensate of the titanium alkoxide, for example. A part of an alkoxy group of the titanium alkoxide may remain in an unreacted state in the particle.

The untreated titanium oxide aerogel particle may contain a small amount of a metallic element other than titanium such as silicon and aluminum. In a case of containing a silicon element, 0.05 or less element ratio Si/Ti of silicon and titanium does not influence the effect of expressing a high level of the photocatalytic function in the visible light region of the titanium oxide aerogel particle.

A crystal structure of the titanium oxide aerogel particle may be any one of a brookite type, an anatase type, and a rutile type, and may have a single crystal structure thereof, and may have a mixed-crystal structure in which these crystals coexist. The crystal structure of the titanium oxide aerogel particle may be controlled by adjusting a low and high degree of a temperature in the heating treatment.

The method for manufacturing the untreated titanium oxide aerogel particle will be described in detail. The method therefor is not particularly limited, but for example, a method in which a porous particle containing titanium oxide is obtained by the sol-gel method, is preferable.

The method for manufacturing the untreated titanium oxide aerogel particle preferably has at least the following (1) and (2), for example.

(1) A step of granulating a porous particle containing titanium oxide by the sol-gel method, and preparing a dispersion containing the porous particle and a solvent (dispersion preparation step).

(2) A step of removing the solvent from the dispersion using supercritical carbon dioxide (solvent removing step).

(1) Dispersion Preparation Step

The dispersion preparation step is a step in which, for example, using the titanium alkoxide as a material, the titanium alkoxide is reacted (hydrolysis and condensation) so that titanium oxide is generated, and therefore the dispersion in which the porous particles containing the titanium oxide are dispersed in the solvent is obtained.

Specifically, the dispersion preparation step is a step as below, for example.

The titanium alkoxide is added to an alcohol, an acid aqueous solution is dropwise added thereto under stirring, the titanium alkoxide is reacted to generate the titanium oxide, and therefore a dispersion in which porous particles containing the titanium oxide are dispersed in alcohol (porous particle dispersion) is obtained.

With an amount added of the titanium alkoxide in the dispersion adjust step, a primary particle diameter of the porous particle may be controlled, and as the amount added of the titanium alkoxide becomes larger, the primary particle diameter of the porous particle becomes smaller. A mass ratio of the titanium alkoxide to alcohol is, for example, preferably from 0.04 to 0.65, and more preferably from 0.1 to 0.5.

Examples of the titanium alkoxide used in the dispersion preparation step include tetraalkoxy titanium such as tetramethoxy titanium, tetraethoxy titanium, tetrapropoxy titanium, and tetrabutoxy titanium, an alkoxy titanium chelate obtained by chelating a part of an alkoxy group such as di-i-propoxy bis(ethylacetate)titanium and di-i-propoxy bis(acetylacetonato) titanium, and the like. These may be used alone or in combination of two or more thereof.

The titanium oxide aerogel particle may contain a small amount of a metallic element other than titanium such as silicon and aluminum. In this case, tetraalkoxysilane such as tetramethoxysilane, tetraethoxysilane, tetrapropoxysilane, and tetrabutoxysilane, alkyltrialkoxysilane such as methyltrimethoxysilane, methyltriethoxysilane, and ethyltriethoxysilane, dialkyldialkoxysilane such as dimethyldimethoxysilane and dimethyldiethoxysilane, aluminum alkoxide such as aluminum isopropoxide, or the like may be used, and in a case of containing silicon elements, 0 to 0.05 element ratio Si/Ti of silicon and titanium may be used.

Examples of the alcohol used in the dispersion preparation step include methanol, ethanol, propanol, butanol, and the like. These may be used alone or in combination of two or more thereof.

Examples of the acid of the acid aqueous solution used in the dispersion preparation step include an oxalic acid, an acetic acid, a hydrochloric acid, a nitric acid, and the like. An acid concentration of the acid aqueous solution is, for example, preferably from 0.001% by mass to 1% by mass, and more preferably from 0.005% by mass to 0.01% by mass.

An amount of dropwise addition of the acid aqueous solution in the dispersion preparation step is, for example, preferably from 0.001 parts by mass to 0.1 parts by mass with respect to 100 parts by mass of the titanium alkoxide.

A concentration of solid contents of the porous particle dispersion obtained in the dispersion preparation step is, for example, preferably from 1% by mass to 30% by mass.

(2) Solvent Removing Step

The solvent removing step is a step of allowing the supercritical carbon dioxide to contact with the dispersion containing the porous particles and a solvent so as to remove the solvent. In the solvent removing process by the supercritical carbon dioxide, collapse and clogging of pores of the porous particles are unlikely to occur, compared to a solvent removing process by heating. The solvent removing step is the step of removing the solvent by the supercritical carbon dioxide, and therefore the titanium oxide aerogel particle having the BET specific surface area of 120 $m^2/g$ or larger may be obtained.

Specifically, the solvent removing step is carried out by the following operation, for example.

The porous particle dispersion is put into a sealed reactor, and then liquefied carbon dioxide is introduced therein, and thereafter, a pressure inside the sealed reactor is raised by a high pressure pump while heating the sealed reactor so that carbon dioxide in the sealed reactor becomes a supercritical state. Thereafter, the liquefied carbon dioxide is allowed to flow in the sealed reactor to allow the supercritical carbon dioxide to flow out of the sealed reactor, and therefore the supercritical carbon dioxide circulates in the porous particle dispersion in the sealed reactor. While the supercritical carbon dioxide circulates in the porous particle dispersion, the solvent is dissolved in the supercritical carbon dioxide, and therefore the solvent is removed, accompanied by the supercritical carbon dioxide flowing outside the sealed reactor.

A temperature and a pressure in the sealed reactor are set to be a temperature and a pressure at which the carbon dioxide is caused to become a supercritical state. When a critical point of the carbon dioxide is 31.1° C./7.38 MPa, for example, the temperature and the pressure in the sealed reactor are set to be a temperature from 50° C. to 200° C. and a pressure from 10 MPa to 30 MPa.

Untreated Titanium Compound Aerogel Particle: Untreated Silica-Titania Aerogel Particle In the present disclosure, the silica-titania aerogel particle which has not been subjected to the surface treatment by the organometallic compound will be referred to as the "untreated silica-titania aerogel particle."

The untreated silica-titania aerogel particle contains a silica-titania composite that is a silica-titania composite oxide. For example, it is preferable that a value of the element ratio Si/Ti of the silicon and the titanium is more than 0 and 6 or less.

The value of the element ratio Si/Ti of the silicon and the titanium in the untreated silica-titania aerogel particle is, for example, preferably more than 0 and 6 or less, more preferably from 0.05 to 4, and even more preferably from 0.1 to 3, from the viewpoint of expressing the photocatalytic function in the visible light region.

A BET specific surface area of the untreated silica-titania aerogel particle is, for example, preferably from 200 m$^2$/g to 1200 m$^2$/g, more preferably from 300 m$^2$/g to 1100 m$^2$/g, and even more preferably from 400 m$^2$/g to 1000 m$^2$/g, from the viewpoint of expressing a high level of the photocatalytic function.

A volume average particle diameter of the untreated silica-titania aerogel particle is, for example, preferably from 0.1 μm to 3 μm, more preferably from 0.3 μm to 2.8 μm, and even more preferably from 0.4 μm to 2.5 μm, from the viewpoint of expressing a high level of the photocatalytic function.

For example, it is preferable that the untreated silica-titania aerogel particles are agglomerated particles resulted from primary particles, which contain the silica-titania composite oxide, forming a porous structure, and agglomerating, from the viewpoint of expressing a high level of the photocatalytic function. In this case, an average diameter of the primary particles constituting the untreated silica-titania aerogel particle is, for example, preferably from 1 nm to 90 nm, more preferably from 5 nm to 80 nm, and even more preferably from 10 nm to 70 nm.

A method for manufacturing the untreated silica-titania aerogel particle is not particularly limited, but from a viewpoint of controlling a range of the BET specific surface area to be within the above-described range, a sol-gel method using alkoxy silane and titanium alkoxide as materials is preferable, for example. In regard to the untreated silica-titania aerogel particle manufactured by the sol-gel method, the primary particles agglomerate in a dispersion to form the agglomerated particles having a porous structure, and thus the BET specific surface area within the above-described range may be realized.

The untreated silica-titania aerogel particle is preferably formed of a hydrolytic condensate of the alkoxy silane and the titanium alkoxide, for example. A part of a hydrocarbon group such as an alkoxy group of the alkoxy silane or the titanium alkoxide may remain in an unreacted state in the untreated silica-titania aerogel particle.

A total content of silica components and titania components in the untreated silica-titania aerogel particles is, for example, preferably 80% by mass or more, more preferably 90% by mass or more, and even more preferably 95% by mass or more, with respect to a total mass of the untreated silica-titania aerogel particles.

The method for manufacturing the untreated silica-titania aerogel particle will be described in detail. The method therefor is not particularly limited, but for example, a method in which a porous particle containing the silica-titania composite is obtained by the sol-gel method, is preferable.

The method for manufacturing the untreated silica-titania aerogel particle preferably has at least the following (1') and (2'), for example.

(1') A step of granulating a porous particle containing the silica-titania composite by the sol-gel method, and preparing a dispersion containing the porous particle and a solvent (dispersion preparation step).

(2') A step of removing the solvent from the dispersion using supercritical carbon dioxide (solvent removing step).

(1') Dispersion Preparation Step

The dispersion preparation step is a step in which, for example, using the alkoxy silane and the titanium alkoxide as materials, the alkoxy silane and the titanium alkoxide are reacted (hydrolysis and condensation) so that the silica-titania composite is generated, and therefore the dispersion in which the porous particles containing the silica-titania composite are dispersed in the solvent is obtained. For example, it is preferable that the porous particles are agglomerated particles resulted from primary particles, which contain the silica-titania composite, forming a porous structure, and agglomerating.

Specifically, the dispersion preparation step is a step as below, for example.

The alkoxy silane and the titanium alkoxide are added to an alcohol, an acid aqueous solution is dropwise added thereto under stirring, the alkoxy silane and the titanium alkoxide are reacted to generate the silica-titania composite, and therefore a dispersion in which the porous particles containing the silica-titania composite are dispersed in alcohol (porous particle dispersion) is obtained.

By adjusting a mixing ratio of the alkoxy silane and the titanium alkoxide in the dispersion preparation step, the element ratio Si/Ti of the silicon and titanium in the untreated silica-titania aerogel particle may be controlled.

With a total amount of the alkoxy silane and the titanium alkoxide with respect to an amount of the alcohol in the dispersion preparation step, a particle diameter of the primary particles constituting the untreated silica-titania aerogel particle and a particle diameter of the untreated silica-titania aerogel particle may be controlled. In addition, as the total amount of the alkoxy silane and the titanium alkoxide with respect to the amount of the alcohol becomes large, the particle diameter of the primary particles constituting the untreated silica-titania aerogel particle becomes small, and the particle diameter of the untreated silica-titania aerogel particle becomes large. The total amount of the alkoxy silane and the titanium alkoxide is, for example, preferably from 4 parts by mass to 250 parts by mass, and more preferably from 10 parts by mass to 50 parts by mass with respect to 100 parts by mass of the alcohol.

Examples of the alkoxy silane in the dispersion preparation step include tetraalkoxysilane such as tetramethoxysilane, tetraethoxysilane, tetrapropoxysilane, and tetrabutoxysilane, alkyltrialkoxysilane such as methyltrimethoxysilane, methyltriethoxysilane, and ethyltriethoxysilane, alkyldialkoxysilane such as dimethyldimethoxysilane and dimethyldiethoxysilane, and the like. These may be used alone or in combination of two or more thereof.

Examples of the titanium alkoxide used in the dispersion preparation step include tetraalkoxy titanium such as tetramethoxy titanium, tetraethoxy titanium, tetrapropoxy titanium, and tetrabutoxy titanium, an alkoxy titanium chelate obtained by chelating a part of an alkoxy group such as di-i-propoxy bis(ethyl acetoacetate) titanium and di-i-propoxy bis(acetylacetonato)titanium, and the like. These may be used alone or in combination of two or more thereof.

Examples of the alcohol used in the dispersion preparation step include methanol, ethanol, propanol, butanol, and the like. These may be used alone or in combination of two or more thereof.

Examples of the acid of the acid aqueous solution used in the dispersion preparation step include an oxalic acid, an acetic acid, a hydrochloric acid, a nitric acid, and the like. An acid concentration of the acid aqueous solution is, for example, preferably from 0.001% by mass to 1% by mass, and more preferably from 0.005% by mass to 0.01% by mass.

An amount of dropwise addition of the acid aqueous solution in the dispersion preparation step is, for example preferably from 0.001 parts by mass to 0.1 parts by mass with respect to the total amount of 100 parts by mass of the alkoxy silane and the titanium alkoxide.

A concentration of solid contents of the porous particle dispersion obtained in the dispersion preparation step is, for example, preferably from 1% by mass to 30% by mass.

(2') Solvent Removing Step

The solvent removing step is a step of allowing the supercritical carbon dioxide to contact with the dispersion containing the porous particles and a solvent so as to remove the solvent. In the solvent removing process by the supercritical carbon dioxide, collapse and clogging of pores of the porous particles (particularly, the agglomerated particles resulted from the primary particles forming the porous structure, and agglomerating) are unlikely to occur, compared to a solvent removing process by heating. The solvent removing step is the step of removing the solvent by the supercritical carbon dioxide, and therefore the untreated silica-titania aerogel particle having the BET specific surface area of 200 $m^2/g$ or larger may be obtained.

Specifically, the solvent removing step is carried out by the following operation, for example.

The porous particle dispersion is put into a sealed reactor, and then liquefied carbon dioxide is introduced therein, and thereafter, a pressure inside the sealed reactor is raised by a high pressure pump while heating the sealed reactor so that carbon dioxide in the sealed reactor becomes a supercritical state. Thereafter, the liquefied carbon dioxide is allowed to flow in the sealed reactor to allow the supercritical carbon dioxide to flow out of the sealed reactor, and therefore the supercritical carbon dioxide circulates in the porous particle dispersion in the sealed reactor. While the supercritical carbon dioxide circulates in the porous particle dispersion, the solvent is dissolved in the supercritical carbon dioxide, and therefore the solvent is removed, accompanied by the supercritical carbon dioxide flowing outside the sealed reactor.

A temperature and a pressure in the sealed reactor are set to be a temperature and a pressure at which the carbon dioxide is caused to become a supercritical state. When a critical point of the carbon dioxide is 31.1° C./7.38 MPa, for example, the temperature and the pressure in the sealed reactor are set to be a temperature from 50° C. to 200° C. and a pressure from 10 MPa to 30 MPa.

Organometallic Compound

To the surface of the particle contained in the surface layer in this exemplary embodiment (titanium compound particle in the first exemplary embodiment, and at least one particle selected from the group consisting of the titanium compound particle and titanium compound aerogel particle in the second exemplary embodiment), the organometallic compound is bonded via an oxygen atom. The organometallic compound is, for example, preferably a metallic compound formed of only the metal atom, the carbon atom, the hydrogen atom, and the oxygen atom, from the viewpoint of more easily expressing the visible-light responsiveness.

The organometallic compound is, for example, preferably bonded to the surface of the particle via the oxygen atom O that is directly bonded to the metal atom M in the organometallic compound, that is, preferably bonded to the surface of the particle via the covalent bond of M-O—Ti (or M-O—Si), from the viewpoint of more easily expressing the visible-light responsiveness.

The organometallic compound is, for example, preferably an organometallic compound having the metal atom M and the hydrocarbon group directly bonded to the metal atom M is bonded to the surface via the oxygen atom, from the viewpoint of more easily expressing the visible-light responsiveness. The organometallic compound is, for example, preferably bonded to the surface of the particle via the oxygen atom O that is directly bonded to the metal atom M in the organometallic compound. That is, for example, it is preferable that a structure (hydrocarbon group-M-O—Ti (or hydrocarbon group-M-O—Si)) in which the hydrocarbon group, the metal atom M, the oxygen atom O, and the titanium atom Ti are sequentially linked by a covalent bond, is present on the surface of the particle, from the viewpoint of more easily expressing the visible-light responsiveness.

In a case where the organometallic compound has plural hydrocarbon groups, for example, it is preferable that at least one hydrocarbon group is directly bonded to the metal atom in the organometallic compound.

A state of chemical bonding between atoms in the organometallic compound may be confirmed by performing high resolution analysis (narrow scan analysis) of X-ray photoelectron spectroscopy (XPS).

As the metal atom M of the organometallic compound, for example, silicon, aluminum, or titanium is preferable, silicon or aluminum is more preferable, and silicon is particularly preferable.

Examples of the hydrocarbon group contained in the organometallic compound include a saturated or unsaturated aliphatic hydrocarbon having 1 to 40 carbon atoms (for example, preferably 1 to 20 carbon atoms, more preferably 1 to 18 carbon atoms, even more preferably 4 to 12 carbon atoms, and still more preferably 4 to 10 carbon atoms), and an aromatic hydrocarbon having 6 to 27 carbon atoms (for example, preferably 6 to 20 carbon atoms, more preferably 6 to 18 carbon atoms, even more preferably 6 to 12 carbon atoms, and still more preferably 6 to 10 carbon atoms).

The hydrocarbon group contained in the organometallic compound is, for example, preferably the aliphatic hydrocarbon, more preferably the saturated aliphatic hydrocarbon, and particularly preferably an alkyl group, from viewpoints of expressing a high level of the photocatalytic function and improving the dispersibility. The aliphatic hydrocarbon may be either linear, branched, or cyclic, but is, for example, preferably linear or branched, from the viewpoint of the dispersibility. The number of carbon atoms of the aliphatic hydrocarbon is, for example, preferably from 1 to 20 preferably, more preferably from 1 to 18, even more preferably 4 to 12, and still more preferably from 4 to 10.

As the organometallic compound, for example, a silane compound having the hydrocarbon group is particularly preferable. Examples of the silane compound having the hydrocarbon group include a chlorosilane compound, an alkoxysilane compound, a silazane compound (such as hexamethyldisilazane), and the like.

The silane compound having the hydrocarbon group, which is used in the surface treatment of the untreated particle is, for example, preferably an $R^1{}_nSiR^2{}_m$ compound represented by Formula (1), from the viewpoints of exhibiting a high level of the photocatalytic function and improving the dispersibility.

In $R^1{}_nSiR^2{}_m$ of Formula (1), $R^1$ represents a saturated or unsaturated aliphatic hydrocarbon having 1 to 20 carbon atoms, or an aromatic hydrocarbon having 6 to 20 carbon atoms, $R^2$ represents a halogen atom or an alkoxy group, n represents an integer of 1 to 3, and m represents an integer of 1 to 3, provided that n+m=4. In a case where n is an integer of 2 or 3, plural $R^1$'s may be the same groups, or may be different groups. In a case where m is an integer of 2 or 3, plural $R^2$'s may be the same groups, or may be different groups.

The aliphatic hydrocarbon represented by $R^1$ may be either linear, branched, or cyclic, but is, for example, preferably linear or branched, from the viewpoint of the dispersibility. The number of carbon atoms of the aliphatic hydrocarbon is, for example, preferably from 1 to 20 preferably, more preferably from 1 to 18, even more preferably 4 to 12, and still more preferably from 4 to 10, from the viewpoints of expressing a high level of the photocatalytic function and improving the dispersibility. The aliphatic hydrocarbon may be either saturated or unsaturated, but is, for example preferably the saturated aliphatic hydrocarbon, and more preferably an alkyl group, from the viewpoints of expressing a high level of the photocatalytic function and improving the dispersibility.

Examples of the saturated aliphatic hydrocarbon include linear alkyl groups (such as a methyl group, an ethyl group, a propyl group, a butyl group, a pentyl group, a hexyl group, a heptyl group, an octyl group, a nonyl group, a decyl group, a dodecyl group, a hexadecyl group, and an icosyl group), branched alkyl groups (such as an isopropyl group, an isobutyl group, an isopentyl group, a neopentyl group, a 2-ethylhexyl group, a tertiary butyl group, a tertiary pentyl group, and an isopentadecyl group), cyclic alkyl groups (such as a cyclopropyl group, a cyclopentyl group, a cyclohexyl group, a cycloheptyl group, a cyclooctyl group, a tricyclodecyl group, a norbornyl group, and an adamantyl group), and the like.

Examples of the unsaturated aliphatic hydrocarbon include alkenyl groups (such as a vinyl group (an ethenyl group), a 1-propenyl group, a 2-propenyl group, a 2-butenyl group, a 1-butenyl group, a 1-hexenyl group, a 2-dodecenyl group, and a pentenyl group), alkynyl groups (such as an ethynyl group, a 1-propynyl group, a 2-propynyl group, a 1-butynyl group, a 3-hexynyl group, and a 2-dodecynyl group), and the like.

The aliphatic hydrocarbon includes a substituted aliphatic hydrocarbon. Examples of a substituent that may be substituted on the aliphatic hydrocarbon include a halogen atom, an epoxy group, a glycidyl group, a glycidoxy group, a mercapto group, a methacryloyl group, an acryloyl group, and the like.

The aromatic hydrocarbon represented by $R^1$, for example, preferably has 6 to 20 carbon atoms, more preferably 6 to 18 carbon atoms, even more preferably 6 to 12 carbon atoms, and particularly preferably 6 to 10 carbon atoms.

Examples of the aromatic hydrocarbon include a phenylene group, a biphenylene group, a terphenylene group, a naphthalene group, an anthracene group, and the like.

The aromatic hydrocarbon includes a substituted aromatic hydrocarbon. Examples of a substituent that may be substituted on the aromatic hydrocarbon include a halogen atom, an epoxy group, a glycidyl group, a glycidoxy group, a mercapto group, a methacryloyl group, an acryloyl group, and the like.

Examples of the halogen atom represented by $R^2$ include a fluorine atom, a chlorine atom, a bromine atom, an iodine atom, and the like. As the halogen atom, a chlorine atom, a bromine atom, or an iodine atom is preferable, for example.

Examples of the alkoxy group represented by $R^2$ include an alkoxy group having 1 to 10 carbon atoms (for example, preferably 1 to 8, more preferably 3 to 8). Examples of the alkoxy group include a methoxy group, an ethoxy group, an isopropoxy group, a t-butoxy group, an n-butoxy group, an n-hexyloxy group, a 2-ethylhexyloxy group, a 3,5,5-trimethylhexyloxy group, and the like. The alkoxy group includes a substituted alkoxy group. Examples of a substituent that may be substituted on the alkoxy group include a halogen atom, a hydroxyl group, an amino group, an alkoxy group, an amido group, a carbonyl group, and the like.

In the $R^1{}_n SiR^2{}_m$ compound represented by Formula (1), $R^1$ is, for example, preferably a compound that is the saturated aliphatic hydrocarbon, from the viewpoints of expressing a high level of the photocatalytic function and improving the dispersibility. In the $R^1{}_n SiR^2{}_m$ compound represented by Formula (1), for example, it is particularly preferable that $R^1$ is the saturated aliphatic hydrocarbon having 1 to 20 carbon atoms, $R^2$ is a halogen atom or an alkoxy group, n is an integer of 1 to 3, and m is an integer of 1 to 3, provided that n+m=4.

Examples of the $R^1{}_n SiR^2{}_m$ compound represented by Formula (1) include a silane compound such as vinyltrimethoxysilane, methyltrimethoxysilane, ethyltrimethoxysilane, propyltrimethoxysilane, butyltrimethoxysilane, hexyltrimethoxysilane, n-octyltrimethoxysilane, decyltrimethoxysilane, dodecyltrimethoxysilane, vinyltriethoxysilane, methyltriethoxysilane, ethyltriethoxysilane, butyltriethoxysilane, hexyltriethoxysilane, decyltriethoxysilane, dodecyltriethoxysilane, phenyltrimethoxysilane, o-methylphenyltrimethoxysilane, p-methylphenyltrimethoxysilane, phenyltriethoxysilane, benzyltriethoxysilane, decyltrichlorosilane, and phenyltrichlorosilane (hereinbefore, n=1 and m=3); dimethyldimethoxysilane, dimethyldiethoxysilane, methylvinyldimethoxysilane, methylvinyldiethoxysilane, diphenyldimethoxysilane, diphenyldiethoxysilane, dimethyldichlorosilane, dichlorodiphenylsilane (hereinbefore, n=2 and m=2); trimethylmethoxysilane, trimethylethoxysilane, trimethylchlorosilane, decyldimethylchlorosilane, triphenylchlorosilane (hereinbefore, n=3 and m=1); and 3-glycidoxypropyltrimethoxysilane, γ-methacryloxypropyltrimethoxysilane, γ-mercaptopropyltrimethoxysilane, γ-chloropropyltrimethoxysilane, γ-aminopropyltrimethoxysilane, γ-aminopropyltriethoxysilane, γ-(2-aminoethyl)aminopropyltrimethoxysilane, γ-(2-aminoethyl)aminopropylmethyldimethoxysilane, γ-glycidyloxypropylmethyldimethoxysilane (hereinbefore, $R^1$ is a compound of the substituted aliphatic hydrocarbon or the substituted aromatic hydrocarbon). The silane compound may be used alone or in combination of two or more thereof.

The hydrocarbon group in the silane compound represented by Formula (1) is, for example, preferably the aliphatic hydrocarbon, more preferably the saturated aliphatic hydrocarbon, and particularly preferably an alkyl group, from the viewpoints of expressing a high level of the photocatalytic function and improving the dispersibility. The hydrocarbon group in the silane compound is, for example, preferably a saturated aliphatic hydrocarbon having 1 to 20 carbon atoms, more preferably a saturated aliphatic hydrocarbon having 1 to 18 carbon atoms, even more preferably a saturated aliphatic hydrocarbon having 4 to 12 carbon atoms, and particularly preferably a saturated aliphatic hydrocarbon having 4 to 10 carbon atoms, from the viewpoints of expressing a high level of the photocatalytic function and improving the dispersibility.

Examples of a compound in which the metal atom of the organometallic compound is aluminum include alkylaluminate such as triethoxyaluminum, tri-i-propoxyaluminum, and tri-sec-butoxyaluminum; aluminum chelate such as di-i-propoxy-mono-sec-butoxy aluminum and di-i-propoxy aluminum-ethyl acetoacetate; aluminate-based coupling agents such as acetoalkoxy-aluminum-diisopropylate; and the like.

Examples of a compound in which the metal atom of the organometallic compound is titanium include titanate-based coupling agents such as isopropyl triisostearoyl titanate, tetraoctyl bis(ditridecyl phosphite) titanate, and bis(dioctyl pyrophosphate) oxyacetate titanate; titanium chelate such as di-i-propoxy bis(ethyl acetoacetate) titanium, di-i-propoxy bis(acetylacetonato)titanium, di-i-propoxy bis(triethanolaminate) titanium, di-i-propoxytitanium diacetate, di-i-propoxytitanium dipropionate; and the like.

The organometallic compound may be used alone or in combination of two or more thereof.

The particle of which the organometallic compound is bonded to the surface (particularly, titanium compound aerogel particle of which the organometallic compound is bonded to the surface) is, for example, also preferable from the following viewpoint, in addition to a high level of the photocatalytic function expressed in the visible light region.

Generally, dispersibility of particles in a resin or a solvent is poor, and therefore homogeneity of a coated film becomes low, and the photocatalytic function tends to become unlikely to be exhibited.

With respect to the above description, the particle of which the organometallic compound is bonded to the surface has, on the surface thereof, the hydrocarbon group derived from the organometallic compound, and therefore the dispersibility in the resin or the solvent becomes favorable. Therefore, a coated film that is almost homogenous may be formed, light efficiently reaches the particles, and thus the photocatalytic function becomes likely to be exhibited. In addition, in a case of coating a surface of an outer wall material, a plate, a pipe, a nonwoven fabric, or the like with a paint containing the particles, an agglomeration or a coating defect of the particles is suppressed, and the photocatalytic function becomes likely to be exhibited for a long period of time.

Method for Manufacturing Particle and Surface Treatment Method

A method for manufacturing the particle contained in the surface layer in this exemplary embodiment (titanium compound particle in the first exemplary embodiment, and at least one particle selected from the group consisting of the titanium compound particle and titanium compound aerogel particle in the second exemplary embodiment), is not particularly limited. For example, the particle of this exemplary embodiment may be obtained by surface-treating the untreated particle with the organometallic compound.

Hereinafter, an example of the method for manufacturing the particle of this exemplary embodiment will be described.

The method for manufacturing the particle of this exemplary embodiment is not particularly limited, but preferably includes (a) step of surface-treating the untreated particle with the organometallic compound, and (b) step of heating-treating the particle during or after the step of surface-treating the untreated particle, for example.

(a) Surface Treatment Step

The method of surface-treating the untreated particle with the organometallic compound is not particularly limited, but examples thereof include a method for allowing the organometallic compound itself to directly come into contact with the untreated particle; and a method for allowing the untreated particle to come into contact with a treatment liquid in which the organometallic compound is dissolved in a solvent. Specific examples thereof include a method for adding the organometallic compound itself or a treatment liquid to a dispersion in which the untreated particles are dispersed in a solvent under stirring; and a method for adding (dropwise adding, spraying, and the like) the organometallic compound itself or the treatment liquid to the untreated particle which is in a flowing state by stirring or the like by HENSCHEL MIXER or the like. According to these methods, a reactive group (for example, hydrolyzable groups such as a halogeno group and an alkoxy group) in the organometallic compound is allowed to react with a hydroxyl group present on the surface of the untreated particle, and therefore the untreated particle is surface-treated.

In a case of subjecting the untreated titanium compound aerogel particle to the surface treatment as the untreated particle, the surface treatment step may be carried out in an atmosphere or under a nitrogen atmosphere, but, for example, it is preferable to carry out the surface treatment step in supercritical carbon dioxide. As a result, the organometallic compound reaches the deep inside of pores of the porous particle, and the surface treatment is carried out deep into the pores of the porous particle, and it is preferable to carry out the surface treatment in the supercritical carbon dioxide, for example.

In a case of surface-treating the untreated titanium compound aerogel particle, the surface treatment step is carried out by, for example, a method for mixing the organometallic compound and the porous particle in the supercritical carbon dioxide under stirring so as to be reacted with each other, or a method for preparing a treatment liquid obtained by mixing the organometallic compound and a solvent, and mixing the porous particle and the treatment liquid in the supercritical carbon dioxide under stirring, but in order to obtain a high level of the BET specific surface area while maintaining a pore structure of the porous particle, for example, a method in which the organometallic compound is subsequently put into the supercritical carbon dioxide after a completion of the solvent removing step described above, and the organometallic compound is allowed to react with the surface of the porous particle in the supercritical carbon dioxide, is preferable.

Examples of the solvent for dissolving the organometallic compound include an organic solvent (for example, a hydrocarbon-based solvent, an ester-based solvent, an ether-based solvent, a halogen-based solvent, an alcohol-based solvent, and the like), water, a mixed solvent thereof, and the like. Examples of the hydrocarbon-based solvent include toluene, benzene, xylene, hexane, octane, hexadecane, cyclohexane, and the like. Examples of the ester-based solvent include methyl acetate, ethyl acetate, isopropyl acetate, amyl acetate, and the like. Examples of the ether-based solvent include dibutyl ether, dibenzyl ether, and the like. Examples of the halogen-based solvent include 1,1-dichloro-1-fluoroethane, 1,1-dichloro-2,2,2-trifluoroethane, 1,1-dichloro-2,2,3,3,3-pentafluoropropane, chloroform, dichloroethane, carbon tetrachloride, and the like. Examples of the alcohol-based solvent include methanol, ethanol, i-propyl alcohol, and the like. Examples of water include tap water, distilled water, pure water, and the like. As the solvent, in addition to those described above, other solvents such as dimethylformamide, dimethylacetamide, dimethyl sulfoxide, acetic acid, sulfuric acid, and the like may be used.

In the treatment liquid in which the organometallic compound is dissolved in the solvent, a concentration of the organometallic compound is, for example, preferably from 0.05 mol/L to 500 mol/L, and more preferably from 0.5 mol/L to 10 mol/L.

Conditions for surface-treating the particle with the organometallic compound are, for example, preferably the following conditions, from the viewpoints of expressing a high level of the photocatalytic function and improving the dispersibility. For example, it is preferable that the surface treatment is carried out on the untreated particle with the organometallic compound of from 10% by mass to 100% by mass (for example, preferably from 20% by mass to 75% by mass, and more preferably from 25% by mass to 50% by mass). In a case where an amount of the organometallic compound is 10% by mass or more, a high level of the photocatalytic function is likely to be expressed even in the visible light region, and the dispersibility is also likely to be improved. In a case where the amount of the organometallic compound is 100% by mass or less, an amount of metal derived from the organometallic compound, which is present on the surface of the particle is suppressed from becoming excessive, and therefore a deterioration in the photocatalytic function due to remaining metal is suppressed.

A temperature in the surface treatment of the untreated particle with the organometallic compound is, for example, preferably from 15° C. to 150° C., and more preferably from 20° C. to 100° C. A time of the surface treatment is, for example, preferably from 10 minutes to 120 minutes, and more preferably from 30 minutes to 90 minutes.

In a case of carrying out the surface treatment in the supercritical carbon dioxide, a temperature and a pressure in the surface treatment step are set to be a temperature and a pressure at which the carbon dioxide is caused to become a supercritical state. For example, the surface treatment step is carried out under an atmosphere of a temperature from 50° C. to 200° C. and a pressure from 10 MPa to 30 MPa. A reaction time is, for example, preferably from 10 minutes to 24 hours, more preferably from 20 minutes to 120 minutes, and even more preferably from 30 minutes to 90 minutes.

After surface-treating the untreated particle with the organometallic compound, for example, it is preferable that a drying treatment is carried out. A method for the drying treatment is not particularly limited, and for example, a known drying method such as a vacuum drying method and a spray drying method is applied. A drying temperature is, for example, preferably from 20° C. to 150° C.

In the case of carrying out the surface treatment in the supercritical carbon dioxide, a step of removing a solvent from a dispersion containing the porous particle by using the supercritical carbon dioxide is preferable, and a step of allowing the supercritical carbon dioxide to circulate in the porous particle dispersion subsequently after a completion of the surface treatment step, and thereby removing the solvent, is more preferable, although there is no particular limitation.

(b) Step of Heating Treatment

The heating treatment is carried out during the step of surface-treating the untreated particle, or after the step of surface-treating the untreated particle.

The heating treatment may be carried out when surface-treating the untreated particle with the organometallic compound; when performing the drying treatment after the surface treatment; or separately after the drying treatment. From a viewpoint of sufficient reaction of the particle and the organometallic compound before the heating treatment, the heating treatment is, for example, preferably carried out when performing the drying treatment after the surface treatment, or separately after the drying treatment, and from a viewpoint of appropriately performing the drying treatment, the heating treatment is, for example, more preferably carried out separately after the drying treatment.

A temperature in the heating treatment is, for example, preferably from 180° C. to 500° C., more preferably from 200° C. to 450° C., even more preferably from 250° C. to 400° C., from the viewpoints of expressing a high level of the photocatalytic function and improving the dispersibility. A time of the heating treatment is, for example, preferably from 10 minutes to 300 minutes, and more preferably from 30 minutes to 120 minutes, from the viewpoints of expressing a high level of the photocatalytic function and improving the dispersibility. In a case of carrying out the heating treatment during the step of surface-treating the untreated particle, for example, it is preferable that first, the organometallic compound is sufficiently reacted at the temperature of the surface treatment, and then the heating treatment is carried out at the temperature of the heating treatment. In a case of carrying out the heating treatment in the drying treatment after the surface treatment, the temperature of the drying treatment is set as the temperature of the heating treatment, and the drying treatment is carried out.

With the temperature of the heating treatment being from 180° C. to 500° C., the particle expressing a high level of the photocatalytic function even in the visible light region is efficiently obtained. It is presumed that in a case of performing the heating treatment at the temperature from 180° C. to 500° C., the hydrocarbon group derived from the metallic compound which is present on the surface of the particle appropriately oxidizes, and a part of a C—C bond or a C=C bond changes to a C—O bond or a C=O bond.

The heating treatment is preferably carried out in an atmosphere in which an oxygen concentration (volume %) is from 1% to 21%, for example. By carrying out the heating treatment in this oxygen atmosphere, the oxidation of the hydrocarbon group derived from the metallic compound which is present on the surface of the particle may be appropriately and sufficiently performed. The oxygen concentration (volume %) is, for example, preferably from 3% to 21%, and more preferably from 5% to 21%.

A method for the heating treatment is not particularly limited, and for example, a known heating method such as heating by an electric furnace, a baking furnace (roller hearth kiln, shuttle kiln, and the like), a radiant heating furnace, or the like; and heating by laser light, infrared rays, UV, microwave, or the like is applied.

Through the above-described steps, the particle in this exemplary embodiment may be obtained.

Characteristics of Particle

Spectrum

In the particle contained in the surface layer in this exemplary embodiment, absorption by the particle occurs at wavelengths of 450 nm and 750 nm in a visible absorption spectrum.

In the particle in this exemplary embodiment, for example, the absorption preferably occurs at wavelengths of 450 nm, 600 nm, and 750 nm in the visible absorption spectrum, the absorption more preferably occurs in an entire wavelength range of 450 nm to 750 nm in the visible absorption spectrum, and the absorption particularly preferably occurs at wavelengths in an entire wavelength range of 400 nm to 800 nm in the visible absorption spectrum, from the viewpoint of expressing a high level of the photocatalytic function even in the visible light region.

In regard to the particle in this exemplary embodiment, when an absorbance at a wavelength of 350 nm is taken as 1 in an ultraviolet-visible absorption spectrum, the absorbance at a wavelength of 450 nm is preferably 0.02 or higher (for example, preferably 0.1 or higher and more preferably 0.2 or higher), the absorbance at a wavelength of 600 nm is preferably 0.02 or higher (for example, preferably 0.1 or higher and more preferably 0.2 or higher), and the absorbance at a wavelength of 750 nm is preferably 0.02 or higher (for example, preferably 0.1 or higher and more preferably 0.2 or higher), for example, from the viewpoint of expressing a high level of the photocatalytic function even in the visible light region.

The ultraviolet-visible absorption spectrum may be obtained by the following method. The particles to be measured are dispersed in tetrahydrofuran, and then are applied on a glass substrate and dried at 24° C. in the atmosphere. Using a spectrophotometer (for example, U-4100 manufactured by Hitachi High-Technologies Corporation, scanning speed: 600 nm, slit width: 2 nm, sampling interval: 1 nm), a diffuse reflectance spectrum within a wavelength range of 200 nm to 900 nm in a diffuse reflectance arrangement is measured. Based on the diffuse reflectance spectrum, a theoretical absorbance at each wavelength is obtained by Kubelka-Munk transformation, and therefore the ultraviolet-visible absorption spectrum is obtained.

The particle in this exemplary embodiment preferably has, for example, an absorption peak in a wavenumber range of 2700 $cm^{-1}$ to 3000 $cm^{-1}$ in an infrared absorption spectrum.

Specifically, for example, the particle in this exemplary embodiment preferably has at least one absorption peak in the wavenumber range of 2700 $cm^{-1}$ to 3000 $cm^{-1}$ in the infrared absorption spectrum. The expression "having the absorption peak" means that the absorption in which an absorption intensity (absorbance) is 0.022 or greater (5% of light transmittance) occurs in the particle.

A measurement of the infrared absorption spectrum is performed by a method shown below. First, with respect to the titanium oxide particle to be measured, a measurement sample is produced by a KBr pellet method. Then, the measurement sample is measured by an infrared spectrophotometer (FT-IR-410 manufactured by JASCO Corporation) under conditions of an accumulative number of 300 times and resolution of 4 $cm^{-1}$, in the wavenumber range of 500 $cm^{-1}$ to 4000 $cm^{-1}$, and therefore the infrared absorption spectrum is obtained.

Particle Diameter

In the case where the particle in this exemplary embodiment is the titanium compound particle, a volume average particle diameter thereof is, for example, preferably from 10 nm to 1 μm, more preferably from 10 nm to 200 nm, and even more preferably from 15 nm to 200 nm. In a case where the volume average particle diameter of the particles is 10 nm or larger, the particles are unlikely to agglomerate, and thus the photocatalytic function is likely to be improved. In a case where the volume average particle diameter of the particles is 1 μm or smaller, a ratio of the specific surface area to the amount becomes large, and thus the photocatalytic function is likely to be improved. Therefore, in the case where the volume average particle diameter of the particles is within the above-described range, a high level of the photocatalytic function is likely to be expressed even in the visible light region.

Meanwhile, in the case where the particle in this exemplary embodiment is the titanium compound aerogel particle, the particle preferably has, for example, the porous structure in which the primary particles are gathered. An average primary particle diameter of the titanium compound aerogel particles is, for example, preferably from 1 nm to 120 nm. In the case where the average primary particle diameter is 1 nm or larger, a diameter of pores on the surface of the agglomerated particles resulted from the primary particles forming the porous structure, and agglomerating, becomes an appropriate size, thereby improving the adsorption property of a photolysis target, and thus the photocatalytic function is likely to be expressed even in the visible light region. In the case where the average primary particle diameter is 120 nm smaller, it becomes easy that the primary particles form the porous structure and agglomerate so that an aerogel structure is formed, and thus a high level of the photocatalytic function is likely to be expressed even in the visible light region.

Based on the above-described viewpoint, the average primary particle diameter of the titanium compound aerogel particles is, for example, preferably from 5 nm to 100 nm, and more preferably from 10 nm to 90 nm.

In the case where the particle in this exemplary embodiment is the titanium compound aerogel particle, a volume average particle diameter thereof is, for example, preferably from 0.01 μm to 3 μm. In the case where the volume average particle diameter is 0.01 μm or larger, the primary particles form the porous structure and with a high level of the BET specific surface area, the adsorption property of the photolysis target is likely to be improved. Therefore, a high degree of photocatalytic effect becomes likely to be expressed. In the case where the volume average particle diameter is 3 μm or smaller, less coarse particles are present, and the dispersibility of the titanium oxide aerogel particle in a photocatalytic composition, a photocatalyst, or a structure is improved, and thus the photocatalytic function is improved. Therefore, in the case where the volume average particle diameter of the titanium oxide aerogel particles is within the above-described range, a high level of the photocatalytic function is likely to be expressed even in the visible light region.

Based on the above-described viewpoint, the volume average particle diameter of the titanium compound aerogel particles is, for example, preferably from 0.3 μm to 2.8 μm, and more preferably from 0.5 μm to 2.5 μm.

In the case where the particle in this exemplary embodiment is the titanium compound aerogel particle, a volume-based particle size distribution thereof is, for example, preferably from 1.5 to 10. In the case where the volume-based particle size distribution is 1.5 or larger, the primary particles form the porous structure and with a high level of the BET specific surface area, the adsorption property of the photolysis target is likely to be improved. Therefore, a high degree of the photocatalytic effect becomes likely to be expressed. In the case where the volume-based particle size distribution is 10 or smaller, less coarse particles are present, and the dispersibility of the titanium oxide aerogel particles in a photocatalytic composition, a photocatalyst, or a structure is improved, and thus the photocatalytic function is improved. Therefore, in the case where the volume-based particle size distribution of the titanium oxide aerogel particles is within the above-described range, a high level of the photocatalytic function is likely to be expressed even in the visible light region.

Based on the above-described viewpoint, the volume-based particle size distribution of the titanium compound aerogel particles is, for example, preferably from 2 to 9, and more preferably from 3 to 7.

A method for measuring the average primary particle diameter, the volume average particle diameter, and the volume-based particle size distribution of each particle according to this exemplary embodiment as shown in the section of "Examples" to be described later.

For example, it is particularly preferable that the structure according to the first exemplary embodiment and the second exemplary embodiment (this exemplary embodiment) uses the metatitanic acid particle as the particle to be contained in the surface layer.

Binder Resin

The structure according to the first exemplary embodiment and the second exemplary embodiment (this exemplary embodiment) the binder resin (binder) in the surface layer.

The binder resin (binder) is not particularly limited, and examples thereof include an organic-based binder such as a fluorine-based resin, a silicone-based resin, a polyester-based resin, an acrylic-based resin, a styrene-based resin, an acrylonitrile-styrene copolymer resin, an acrylonitrile-butadiene-styrene copolymer (ABS) resin, an epoxy-based resin, a polycarbonate-based resin, a polyamide-based resin, a polyamine-based resin, a urethane-based resin, a polyether-based resin, a polysulfide-based resin, a polyphenol-based resin, a vinyl chloride-based resin, an olefin-based resin, or a composite thereof, or a silicone-modified or halogen-modified resin thereof. In addition, examples thereof include an inorganic-based binder such as glass, a ceramic, and metal powders.

Among these, for example, an acrylic-based resin, a styrene-based resin, a silicone-based resin, a vinyl chloride-based resin, a urethane-based resin, a polyester-based resin, and an olefin-based resin are preferable, an acrylic-based resin, a styrene-based resin, a silicone-based resin, a vinyl chloride-based resin, and a polyester-based resin are more preferable, an acrylic-based resin, a silicone-based resin, and a vinylchloride-based resin are even more preferable, and a silicone-based resin is still more preferable.

The term "-based" in each resin means that a corresponding resin may be a copolymer resin with another resin, and also means that a content of a component of the corresponding resin is highest in terms of a molar ratio compared to a component of the other resin. That is, in the case of the silicone-based resin, the silicone-based resin is a copolymer resin with another resin component in addition to a homopolymer resin formed of only a component of the silicone resin, the copolymer resin being a resin in which a content of the component of the silicone resin is highest compared to the component of the other resin.

Other Components

The surface layer may contain other components in addition to the components described above. As the other components, a known additive is used, and examples thereof include a promoter, a colorant, a filler, a preservative, an antifoaming agent, an adhesion improver, a thickener, and the like.

Characteristics of Surface Layer

In the surface layer, a mass ratio of the particle and the binder resin is, for example, preferably 18:100 to 95:100, more preferably 35:100 to 75:100, and even more preferably 45:100 to 65:100, from viewpoints of photocatalytic activity, the adsorption property, and the water repellency by the particle surface, and from a viewpoint of fixation by the binder resin.

In the surface layer, for example, it is preferable that the particles are exposed (cueing) on the surface. Specifically, from the viewpoints of the photocatalytic activity, the deodorizing property and the antifouling property by the particle surface, an area proportion in which the particles are exposed on the surface is, for example, preferably from 4% to 18%, more preferably from 6% to and 15%, and even more preferably from 9% to 13%.

The area proportion in which the particles are exposed on the surface layer is measured by the following method.

The titanium compound particles or titanium compound aerogel particles in the binder resin are observed with a scanning electron microscope (SEM) apparatus (S-4100 manufactured by Hitachi, Ltd.) and images thereof are taken, these images are put into an image analyzer (LUZEX III, manufactured by Nireco Corporation), an area of each particle is measured by image analysis of particles, and thus the area proportion of the particles exposed on the surface of the surface layer is calculated. The electron microscope adjusts the particles to have a magnification at which the analysis becomes possible.

Base Material

The base material in each of the first exemplary embodiment and the second exemplary embodiment is not particularly limited, and examples thereof include various materials irrespective of inorganic materials and organic materials, and a shape thereof is also not limited.

As specific examples thereof, the base material described above is preferable, for example.

Manufacturing of Structure

The method for manufacturing the structure according to this exemplary embodiment is not particularly limited, and a method in which a composition for forming the surface layer is prepared, the composition for forming the surface layer is applied to the base material by a known application method, and then is dried to form the surface layer, may be used.

Examples of the application method of the composition for forming the surface layer in this exemplary embodiment include a spin coating method, a dip coating method, a flow coating method, a spray coating method, a roll coating method, a brush painting method, a sponge coating method, a screen printing method, an ink jet printing method, and the like.

For example, water, an organic solvent, and the like are preferably used as a dispersion medium used in the composition for forming the surface layer. Examples of water include tap water, distilled water, pure water, and the like. The organic solvent is not particularly limited, and examples thereof include a hydrocarbon solvent, an ester solvent, an ether solvent, a halogen solvent, an alcohol solvent, and the like. From viewpoints of dispersion stability and preservation stability, the dispersion preferably contains, for example, at least one compound selected from the group consisting of a dispersant and a surfactant. As the dispersant and surfactant, a known chemical substance may be used. The dispersion may contain a binder as an emulsion.

The composition for forming the surface layer may contain one type of the particle or may contain two or more kinds thereof.

A content of the particles in the composition for forming the surface layer is not particularly limited and may be appropriately selected in accordance with various aspects of the dispersion medium, the binder resin, and the like, a desired amount of the photocatalyst, and the like.

EXAMPLES

Hereinafter, the exemplary embodiment of the invention will be described with reference to examples, but the invention is not limited to these examples.

Example 1

Preparation of Metatitanic Acid Slurry

With respect to $TiO_2$ in a titanyl sulfate solution, in terms of $TiO_2$, 8% by mass of anatase seed separately prepared is added to the titanyl sulfate solution in which a $TiO_2$ concentration is 260 g/L, and a $Ti^{3+}$ concentration is 6.0 g/L in terms of $TiO_2$. Next, this solution is heated above a boiling point to hydrolyze titanyl sulfate ($TiOSO_4$), and therefore a particulate metatitanic acid will be generated. Next, the metatitanic acid particles is filtered and washed, and then slurried, and neutralized and washed at pH 7. In this manner, a metatitanic acid slurry having a volume average particle diameter of 42 nm will be obtained.

Preparation of Metatitanic Acid Particles 5N aqueous sodium hydroxide solution is added to the metatitanic acid slurry having the volume average particle diameter of 42 nm while stirring to adjust the pH 8.5, and after being kept stirred for 2 hours, the mixture is neutralized to pH 5.8 with 6N hydrochloric acid, filtered, and washed with water. After washing, water is added thereto to make a slurry again, 6N hydrochloric acid is added thereto while stirring to adjust the pH to 1.3, and the mixture is kept stirred for 3 hours. From this slurry, 100 parts by mass as the metatitanic acid is taken out and kept heated at 60° C., 30 parts by mass of hexyltrimethoxysilane is added thereto while stirring, and after being kept stirred for 30 minutes, 7N aqueous sodium hydroxide solution is added to neutralize the pH to pH 7, and the mixture is filtered and washed with water. A residue after filtration and washing with water is spray-dried by an airflow-type dryer at an outlet temperature of 150° C., and therefore a dry powder will be obtained. A heating treatment is performed on the obtained dry powder at 360° C. for 90 minutes by an electric furnace in which an oxygen concentration (volume %) is set to 12%, and therefore metatitanic acid particles 1 will be obtained.

Production of Structure

Metatitanic acid particles 1:10 parts by mass

Binder resin: silicone resin (manufactured by Shin-Etsu Chemical Co., Ltd., product name: KR-400): 200 parts by mass Dispersion medium: Toluene: 4700 parts by mass The above components are mixed to prepare a composition for forming a surface layer, applied to a base material (backing paper for vinyl wallpaper) by a spin coating method, and dried (160° C., 1 minute), and therefore a structure (test piece) will be obtained.

Examples 2 to 15

Structures (test pieces) are produced in the same manner as in Example 1, except that the material (core) of the particles, the treatment conditions (surface treatment and heating treatment), the formulation ratio of the particles and the binder resin, and the area proportion of the exposed particles are changed as described in Tables 1 and 2.

Comparative Examples 1 and 2

Structures (test pieces) are produced in the same manner as in Example 1, except that the material (core) of the particles, the treatment conditions (surface treatment and heating treatment), the formulation ratio of the particles and the binder resin, and the area proportion of the exposed particles are changed as described in Tables 1 and 2.

Measurement of Physical Property

With respect to each particle obtained in each example, each physical property is measured according to the following measurement method. The results are shown in Table 2.

BET Specific Surface Area

Using "MACSORB HM model-1201" manufactured by MOUNTECH Co., Ltd. as a specific surface area measuring device, 50 mg of a sample is pretreated at 30° C. for 120 minutes for degassing, and therefore a BET specific surface area is determined by a BET multipoint method using nitrogen gas with a purity of 99.99% or higher.

Water Contact Angle

The test piece is left still for 24 hours or longer in an environment of a temperature of 25° C. and a relative humidity of 60% and subjected to humidity conditioning, and then 2 µL droplets of deionized water are injected to the surface of the test piece with a syringe under the same environment of the temperature and the humidity, and a water contact angle after 30 seconds is measured by a θ/2 method using a contact angle meter. The measurement is performed by using a model number CA-XP manufactured by Kyowa Interface Science Co., Ltd. as the contact angle meter.

Measurement of Volume Average Particle Diameter in Case Where Particles are Titanium Compound Particles The volume average particle diameter of the particles is measured by using a dynamic light scattering particle size measuring apparatus (for example, NANOTRACK UPA-ST manufactured by MicrotracBEL Corp.). For the measurement conditions, a concentration of the sample is set to 20% and a measurement time is set to 300 seconds. The dynamic light scattering particle size measuring apparatus is an apparatus that measures a particle diameter by utilizing the Brownian motion of a dispersoid, by which a particle diameter is measured by irradiating a solution with a laser beam and detecting scattered light. Based on the particle size distribution measured by the dynamic light scattering particle size measuring apparatus, an accumulative distribution is drawn from a small diameter side of each individual particle volume with respect to a divided particle size range (channel), and a particle diameter with 50% accumulation will be determined as the volume average particle diameter D50v.

Measurement of Average Primary Particle Diameter in Case where Particles are Titanium Compound Aerogel Particles An average primary particle diameter is measured as follows. With respect to 100 parts by mass of resin particles having a volume average particle diameter of 8 µm (styrene-butyl acrylate copolymer particles: copolymerization ratio (mass ratio)=80:20, weight-average molecular weight Mw=130000, glass transition temperature Tg=59° C.), 1.0 part by mass of the titanium compound aerogel particles are mixed and blended at 13000 rpm for 2 minutes by using a sample mill (model SK-M2 type) (manufactured by Kyoritsu Riko Co., Ltd.). The titanium compound aerogel particles obtained by dispersing the titanium compound aerogel particles in the resin particles are observed with a scanning electron microscope (SEM) apparatus (S-4100 manufactured by Hitachi, Ltd.) and images thereof are taken, these images are put into an image analyzer (LUZEX III, manufactured by Nireco Corporation), an area of each particle is measured by image analysis of primary particles, an equivalent circle diameter is calculated from this area value, and an average obtained is used as an average primary particle diameter. With the electron microscope, the primary particles are adjusted to a magnification at which the image analysis became possible, and about 10 to 50 primary particles are analyzed, and therefore an average primary particle diameter will be determined. In the determination of the primary particle diameter, particles that form agglomerated titanium compound aerogel particles are defined as the primary particles, and are subjected to the image analysis.

Measurement of Volume Average Particle Diameter in Case where Particles are Titanium Compound Aerogel Particles A volume average particle diameter is measured as follows. With respect to 100 parts by mass of resin particles having a volume average particle diameter of 8 μm (styrene-butyl acrylate copolymer particles: copolymerization ratio (mass ratio)=80:20, weight-average molecular weight Mw=130000, glass transition temperature Tg=59° C.), 1.0 part by mass of the titanium compound aerogel particles are mixed and blended at 13000 rpm for 2 minutes by using a sample mill (model SK-M2 type) (manufactured by Kyoritsu Riko Co., Ltd.). 0.1 g of titanium compound-containing resin particles after being blended is put in a beaker, 1.5 g of an aqueous surfactant solution in which an anionic surfactant (TAYCA POWER BN2060, manufactured by TAYCA CORPORATION) is diluted with deionized water by 12%, is added thereto, and after sufficiently wetting the particles, 5 g of pure water is added thereto, followed by dispersion for 30 minutes by an ultrasonic disperser, the resin particles are removed with 5C filter paper, and therefore a titanium compound aerogel particle dispersion will be obtained. A volume average particle diameter of the titanium compound aerogel particles in the titanium compound aerogel particle dispersion is measured and determined by NANOTRACK UPA-ST (dynamic light ovulation type particle size measuring apparatus manufactured by MicrotracBEL Corp.).

Specifically, an accumulative distribution is drawn from a small diameter side of each individual particle volume with respect to a particle size range in which the particle size distribution is divided (channel), and a particle diameter with 50% accumulation is determined as the volume average particle diameter (particle diameter D50v).

Volume-Based Particle Size Distribution

A volume-based particle size distribution is measured as follows. The volume-based particle size distribution is measured in the same manner as the volume average particle diameter. An accumulative distribution is drawn from a small diameter side of each individual particle volume with respect to a particle size range in which the particle size distribution is divided (channel), and a square root of the value obtained by dividing a particle diameter D90v with 90% accumulation by a particle diameter D10v with 10% accumulation is defined as a volume-based particle size distribution (GSDv). That is, the volume-based particle size distribution (GSDv)=(D90v/D10v)$^{0.5}$.

Ultraviolet-Visible Absorption Spectrum

The particles obtained in each example are dispersed in tetrahydrofuran, and then are applied on a glass substrate and dried at 24° C. in the atmosphere. A spectrophotometer (for example, U-4100 manufactured by Hitachi High-Technologies Corporation) is used, and a scanning speed: 600 nm, a slit width: 2 nm, a sampling interval: 1 nm are respectively set, and therefore a diffuse reflectance spectrum within a wavelength range of 200 nm to 900 nm in a diffuse reflectance arrangement is measured. Based on the diffuse reflectance spectrum, a theoretical absorbance at each wavelength will be obtained by Kubelka-Munk transformation, and therefore the ultraviolet-visible absorption spectrum will be obtained.

Performance Evaluation

Photocatalytic Activity

As a photocatalytic activity of metatitanic acid particles in the visible light region, degradability (chromaticity variation) of an ink is evaluated as described below.

The metatitanic acid particles obtained in each example are dispersed in water containing 4% by mass of methanol so that a concentration of solid contents became 2% by mass, and then the dispersion is applied by spraying to a tile (5 cm square) and then dried, and therefore the metatitanic acid particles are uniformly adhered to a surface of the tile. Subsequently, a diluted ink in which a fountain pen ink (INK-30-R, manufactured by Pilot Corporation) is diluted 15 times with a methanol-water mixed solution (methanol: water=3:5), is sprayed to be applied on the surface of the tile, and then dried, and therefore a test piece will be prepared.

Light emitting diode (LED) which radiates visible light with a wavelength from 400 nm to 800 nm is used (however, an absorption wavelength range of the ink (wavelength from 450 nm to 550 nm) is cut with a filter), and the test piece is continuously irradiated with visible light (10000 LX (lux)) for 2 hours immediately after the preparation of the test piece. In this case, a 5 yen coin is placed on a center portion of the irradiated surface of the test piece, and thus an irradiation-shielded portion will be formed.

Hues of the test piece immediately after the preparation and the test piece after being irradiated with visible light for 2 hours are measured with a spectrocolorimeter (RM200QC manufactured by X-Rite), and thus ΔE1 and ΔE2 calculated by the following formula are obtained. The chromaticity E is a value calculated by E={(L*)$^2$+=(a*)$^2$+(b*)$^2$}$^{0.5}$, and L*, a*, and b* are coordinate values of the L*a*b* color system.

ΔE1=chromaticity of irradiated surface after continuous irradiation with visible light for 2 hours−chromaticity of one side of test piece immediately after preparation ΔE2=chromaticity of irradiation-shielded surface after continuous irradiation with visible light for 2 hours−chromaticity of one side of test piece immediately after preparation From ΔE1 and ΔE2, a decolorization variation value ΔE=ΔE1−ΔE2 will be obtained, and the degradability is evaluated based on ΔE as described below.

A: Very good degradability

B: Good degradability

C: Slightly good degradability

D: Poor degradability

Deodorizing Property

First, 1 m$^2$ test piece is placed in 300 L space, the residual air in the interior is exhausted entirely from the space with an aspirator, and then ammonia gas having 50 ppm concentration is injected. Subsequently, the space containing the test piece is continuously irradiated with visible light (6000 LX (lux) on the surface of the test piece) by using a light emitting diode (LED) which radiated visible light having a wavelength from 400 nm to 800 nm.

The concentration of ammonia gas in the space after continuous irradiation with visible light for 2 hours is measured using a detector tube (manufactured by GASTEC CORPORATION), and the deodorizing property is evaluated by a reduction rate of the ammonia gas.

A: 90%≤ammonia reduction rate, very good deodorizing property

B: 70%≤ammonia reduction rate<90%, good deodorizing property

C: 50%≤ammonia reduction rate<70%, slightly good deodorizing property

D: ammonia reduction rate<50%, poor deodorizing property

Antifouling Property

As a contaminant, 5 parts by mass of a solution in which 5 parts by mass of carbon powder is suspended in a mixed solution of 40 parts by mass of water and 45 parts by mass of ethanol, is applied to a range of 25±1 mm×40±1 mm of the test piece. After preserving the test piece in an atmosphere at 40° C. for 1 hour, a contaminated site is washed with 50 parts by mass of a mixed solution of 50 parts by mass of water and 50 parts by mass of ethanol, and evaluation will be performed according to the following indices.

A: A level not distinguishable from a level before the application of the contaminant
B: Trace of contamination is less than 5% with respect to the area to which the contaminant is applied
C: Trace of contamination is 5% or more and less than 25% with respect to the area to which the contaminant is applied
D: Trace of contamination is 25% or more with respect to the area to which the contaminant is applied

TABLE 1

| | | Surface treatment Metallic compound | | Heating treatment | | |
|---|---|---|---|---|---|---|
| | Core | Type | Amount [parts by mass] | Temperature [° C.] | Time [min.] | Oxygen concentration [volume %] |
| Example 1 | Metatitanic acid | Hexyltrimethoxysilane | 15 | 360 | 90 | 20 |
| Example 2 | Titanium oxide | Hexyltrimethoxysilane | 15 | 360 | 90 | 20 |
| Example 3 | Silica titanium aerogel | Hexyltrimethoxysilane | 15 | 360 | 90 | 20 |
| Example 4 | Metatitanic acid | Hexyltrimethoxysilane | 20 | 360 | 90 | 20 |
| Example 5 | Metatitanic acid | Hexyltrimethoxysilane | 8 | 360 | 90 | 20 |
| Example 6 | Metatitanic acid | Hexyltrimethoxysilane | 25 | 360 | 90 | 20 |
| Example 7 | Metatitanic acid | Hexyltrimethoxysilane | 15 | 500 | 90 | 20 |
| Example 8 | Metatitanic acid | Hexyltrimethoxysilane | 15 | 180 | 90 | 20 |
| Example 9 | Titanium aerogel | Hexyltrimethoxysilane | 15 | 360 | 90 | 20 |
| Example 10 | Metatitanic acid | Hexyltrimethoxysilane | 15 | 360 | 90 | 20 |
| Example 11 | Metatitanic acid | Hexyltrimethoxysilane | 15 | 360 | 90 | 20 |
| Example 12 | Metatitanic acid | Hexyltrimethoxysilane | 15 | 360 | 90 | 20 |
| Example 13 | Metatitanic acid | Hexyltrimethoxysilane | 15 | 360 | 90 | 20 |
| Example 14 | Metatitanic acid | Hexyltrimethoxysilane | 15 | 360 | 90 | 20 |
| Example 15 | Metatitanic acid | Hexyltrimethoxysilane | 15 | 360 | 90 | 20 |
| Comparative Example 1 | Titanium oxide | Hexyltrimethoxysilane | 15 | 360 | 90 | 20 |
| Comparative Example 2 | Silica titanium aerogel | Hexyltrimethoxysilane | 15 | 360 | 90 | 20 |

TABLE 2

| | | | Area proportion of exposed particles [%] | UV-Vis characteristic | | | Physical property | | Performance evaluation | | |
|---|---|---|---|---|---|---|---|---|---|---|---|
| | D50v [μm] | Formulation ratio of resin particles | | Absorbance at 450 nm | Absorbance at 600 nm | Absorbance at 750 nm | BET specific surface area [m²/g] | Water contact angle [deg.] | Photocatalytic activity | Deodorizing property | Antifouling property |
| Example 1 | 0.042 | 50:100 | 10 | 0.63 | 0.46 | 0.29 | 180 | 110 | A | A | B |
| Example 2 | 12 | 50:100 | 9 | 0.56 | 0.41 | 0.24 | 160 | 110 | A | B | B |
| Example 3 | 1.05 | 50:100 | 10 | 0.59 | 0.43 | 0.26 | 980 | 110 | A | A | B |
| Example 4 | 0.042 | 50:100 | 13 | 0.6 | 0.45 | 0.3 | 135 | 140 | A | B | A |
| Example 5 | 0.042 | 50:100 | 12 | 0.57 | 0.42 | 0.3 | 175 | 90 | A | B | C |
| Example 6 | 0.042 | 50:100 | 11 | 0.6 | 0.46 | 0.3 | 135 | 180 | A | C | B |
| Example 7 | 0.042 | 50:100 | 9 | 0.28 | 0.19 | 0.11 | 195 | 90 | C | B | C |
| Example 8 | 0.042 | 50:100 | 10 | 0.35 | 0.18 | 0.1 | 150 | 90 | C | B | C |
| Example 9 | 2.8 | 50:100 | 8 | 0.55 | 0.39 | 0.24 | 870 | 100 | B | A | C |
| Example 10 | 0.015 | 50:100 | 10 | 0.57 | 0.37 | 0.25 | 160 | 110 | B | A | B |
| Example 11 | 0.042 | 95:100 | 16 | 0.63 | 0.48 | 0.3 | 155 | 110 | A | A | A |
| Example 12 | 0.042 | 18:100 | 7 | 0.53 | 0.34 | 0.25 | 145 | 110 | B | C | C |
| Example 13 | 0.042 | 50:100 | 18 | 0.63 | 0.48 | 0.3 | 160 | 110 | A | A | A |
| Example 14 | 0.042 | 50:100 | 4 | 0.55 | 0.37 | 0.29 | 160 | 110 | B | C | C |
| Example 15 | 0.042 | 50:100 | 12 | 0.63 | 0.46 | 0.29 | 160 | 110 | A | A | B |
| Comparative Example 1 | 0.15 | 50:100 | 12 | 0.33 | 0.16 | 0.1 | 80 | 25 | C | D | D |
| Comparative Example 2 | 3.6 | 50:100 | 3 | 0.5 | 0.32 | 0.23 | 1250 | 185 | D | D | C |

Based on the results of the performance evaluation shown in Tables 1 and 2, it is understood that the present example in excellent in the photocatalytic activity in the visible light region, and is excellent in the deodorizing property and the antifouling property, as compared to the comparative examples.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments are chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A structure comprising:
    a base material; and
    a surface layer that contains a binder resin and a titanium compound particle having absorption at 450 nm and 750 nm in a visible absorption spectrum and a BET specific surface area within a range of 100 m$^2$/g to 1200 m$^2$/g,
    wherein the titanium compound particle is a metatitanic acid particle.

2. The structure according to claim 1, which is selected from the group consisting of an interior wallpaper, a plaster wall, a tile, and a siding material.

3. The structure according to claim 1,
    wherein the titanium compound particle has a volume average particle diameter within a range of 10 nm to 1 μm.

4. The structure according to claim 1,
    wherein a water contact angle on a surface of the surface layer is within a range of 90 degrees to 180 degrees.

5. The structure according to claim 1,
    wherein absorption by the titanium compound particle occurs within an entire range of a wavelength of 400 nm to 800 nm.

6. The structure according to claim 1,
    wherein the titanium compound particle has an absorption peak within a range of 2700 cm$^{-1}$ to 3000 cm$^{-1}$ in an infrared absorption spectrum.

7. The structure according to claim 1,
    wherein a mass ratio of the titanium compound particle to the binder resin is within a range of 18:100 to 95:100.

8. The structure according to claim 1,
    wherein an area proportion of the titanium compound particle exposed to a surface of the surface layer is within a range of 4% to 18%.

9. The structure according to claim 1,
    wherein the binder resin is selected from the group consisting of an acrylic resin, a styrene resin, a silicone resin, a vinyl chloride resin, a urethane resin, a polyester resin, and an olefin resin.

10. The structure according to claim 1,
    wherein the binder resin is a silicone resin.

11. A structure comprising:
    a base material; and
    a surface layer that contains a binder resin and a particle selected from the group consisting of a metatitanic acid particle and a titanium compound aerogel particle having absorption at 450 nm and 750 nm in a visible absorption spectrum,
    wherein a water contact angle on a surface of the surface layer is within a range of 90 degrees to 180 degrees.

12. The structure according to claim 11, which is selected from the group consisting of an interior wallpaper, a plaster wall, a tile, and a siding material.

13. The structure according to claim 11,
    wherein the titanium compound aerogel particle is a particle selected from the group consisting of a silica-titania aerogel particle and a titanium oxide aerogel particle.

14. The structure according to claim 11,
    wherein the titanium compound aerogel particle has a volume average particle diameter within a range of 0.01 μm to 3 μm.

15. The structure according to claim 11,
    wherein the particle has a BET specific surface area within a range of 100 m$^2$/g to 1200 m$^2$/g.

16. The structure according to claim 11,
    wherein the metatitanic acid particle has an absorption peak within a range of 2700 cm$^{-1}$ to 3000 cm$^{-1}$ in an infrared absorption spectrum.

17. The structure according to claim 11,
    wherein a mass ratio of the metatitanic acid particle to the binder resin is within a range of 18:100 to 95:100.

18. The structure according to claim 11,
    wherein an area proportion of the metatitanic acid particle exposed to a surface of the surface layer is within a range of 4% to 18%.

19. The structure according to claim 11,
    wherein the binder resin is selected from the group consisting of an acrylic resin, a styrene resin, a silicone resin, a vinyl chloride resin, a urethane resin, a polyester resin, and an olefin resin.

* * * * *